United States Patent [19]

Hallewell et al.

[11] Patent Number: 5,252,476
[45] Date of Patent: Oct. 12, 1993

[54] SUPEROXIDE DISMUTASE CLONING AND EXPRESSION IN MICROORGANISMS

[75] Inventors: Robert A. Hallewell, San Francisco; Guy T. Mullenbach, Oakland, both of Calif.

[73] Assignee: Chiron Corporation, Emeryville, Calif.

[21] Appl. No.: 222,352

[22] Filed: Jul. 20, 1988

Related U.S. Application Data

[63] Continuation of Ser. No. 931,920, Nov. 14, 1986, abandoned, which is a continuation of Ser. No. 609,412, May 11, 1984, abandoned, which is a continuation-in-part of Ser. No. 538,607, Oct. 3, 1983, abandoned.

[51] Int. Cl.$^5$ .................. C12N 21/02; C12N 1/19; C12N 15/53; C12N 15/81
[52] U.S. Cl. .................. 435/189; 435/320.1; 435/942; 435/254.21; 435/254.2; 536/23.5; 935/69
[58] Field of Search .................. 435/68, 70, 71, 91, 435/172.1, 172.3, 252.3, 252.31-252.35, 189, 320, 254, 255, 256, 240.1, 240.2; 536/27; 935/14, 19, 21, 28, 29, 60, 69, 73

[56] References Cited

U.S. PATENT DOCUMENTS 4,387,162  6/1983  Aigle et al. .................. 435/256
4,443,539  4/1984  Fraser et al. .................. 435/256

OTHER PUBLICATIONS

Lieman-Hurwitz et al, "Human cytoplasmic superoxide dismutase cDNA clone: A probe for studying the molecular biology of Down syndrome", Proc. Natl. Acad. Sci. USA 79: 2808 (1982).
DeBoer et al, "Construction of a tandem trp-lac promoter and a hybrid trp-las promoter for efficient and controlled expression of the human growth hormone gene in Escherichia coli", in Promoters: Structure and Function, 1982, Praeger Publishers, New York, pp. 462-481.
Guarente et al, "A technique for expressing eukaryotic genes in bacteria", Science 209: 1428 (1980).
Rosenberg et al, "Regulatory sequences involved in the promotion and termination of RNA transcription", Annual Review of Genetics 13: 319 (1979).
Beggs, "Transformation of yeast by a replicating hybrid plasmid", Nature 275: 104 (1978).
Steitz, "Genetic signals and nucleotide sequences in messenger RNA", in Biological Regulation and Development, vol. 1, Goldberger (ed.), 1979, Plenum Press, New York, pp. 349-357.
Maniatis et al; Cell 15: 687 (1978).
Gene Expression, vol. 2, Lewin, 1974, John Wiley & Sons, New York, N.Y., pp. 148-153.
Sherman et al. (1983) Proc. Nat'l. Acad. of SCience, 80:5465-5469.
Hallewell et al. Nucleic Acids Research vol. 13:6:2017-2034 (1985).
Steinman The Journal of Biological Chemistry vol. 255:14:6758-6765 (1980).

Primary Examiner—Richard A. Schwartz
Assistant Examiner—Robert A. Hodges
Attorney, Agent, or Firm—Grant D. Green; Amy L. Collins; Robert P. Blackburn

[57] ABSTRACT

Methods and compositions are provided for the production of human superoxide dismutase and a novel protocol for enhancing efficiency of expression. The gene encoding for human superoxide dismutase is isolated and inserted into a vector in conjunction with a synthetic linker which provides for enhanced efficiency in translation.

E. coli strain D1210 (pSOD×8) was deposited at the A.T.C.C. on Sep. 27, 1983 and given Accession No. 39453. Yeast strain 2150-2-3 (pC1/1GAPSOD) and E. coli strains D1210 (pSOD11) and D1210 (pS2OR) were deposited at the A.T.C.C. on May 9, 1984, and given Accession Nos. 20708, 39679 and 39,680, respectively.

12 Claims, 5 Drawing Sheets

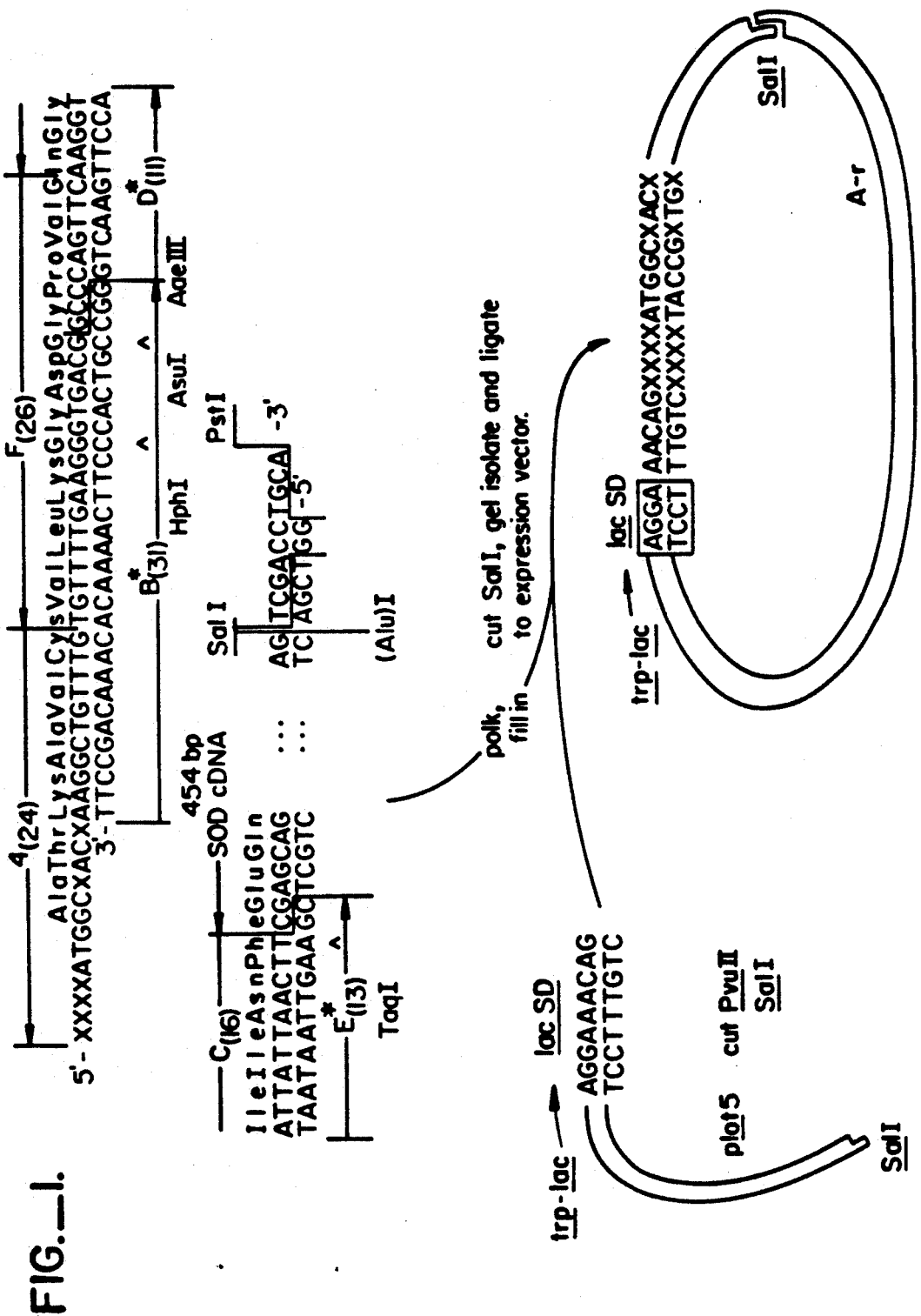
FIG._1.

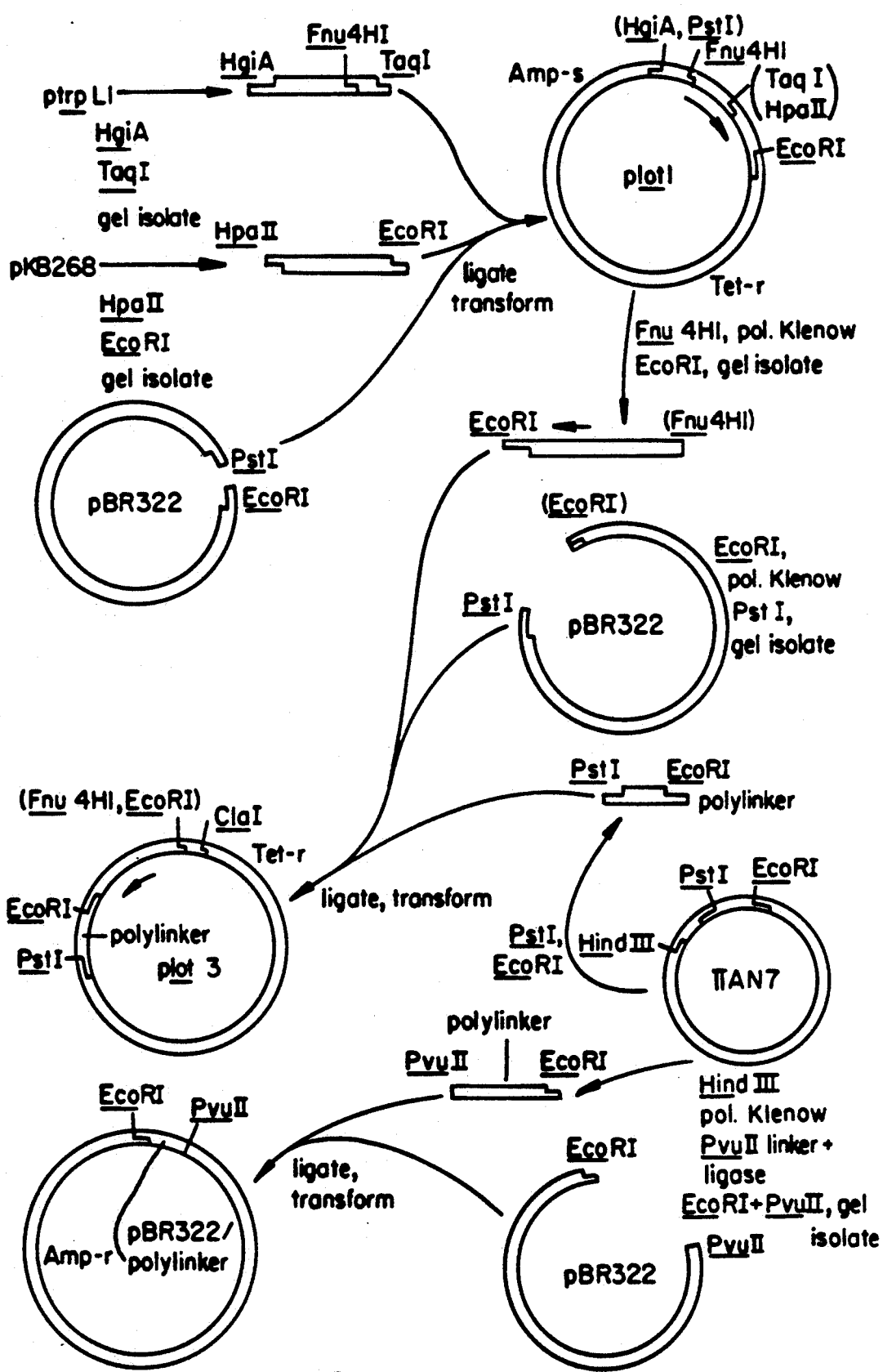
FIG._2.

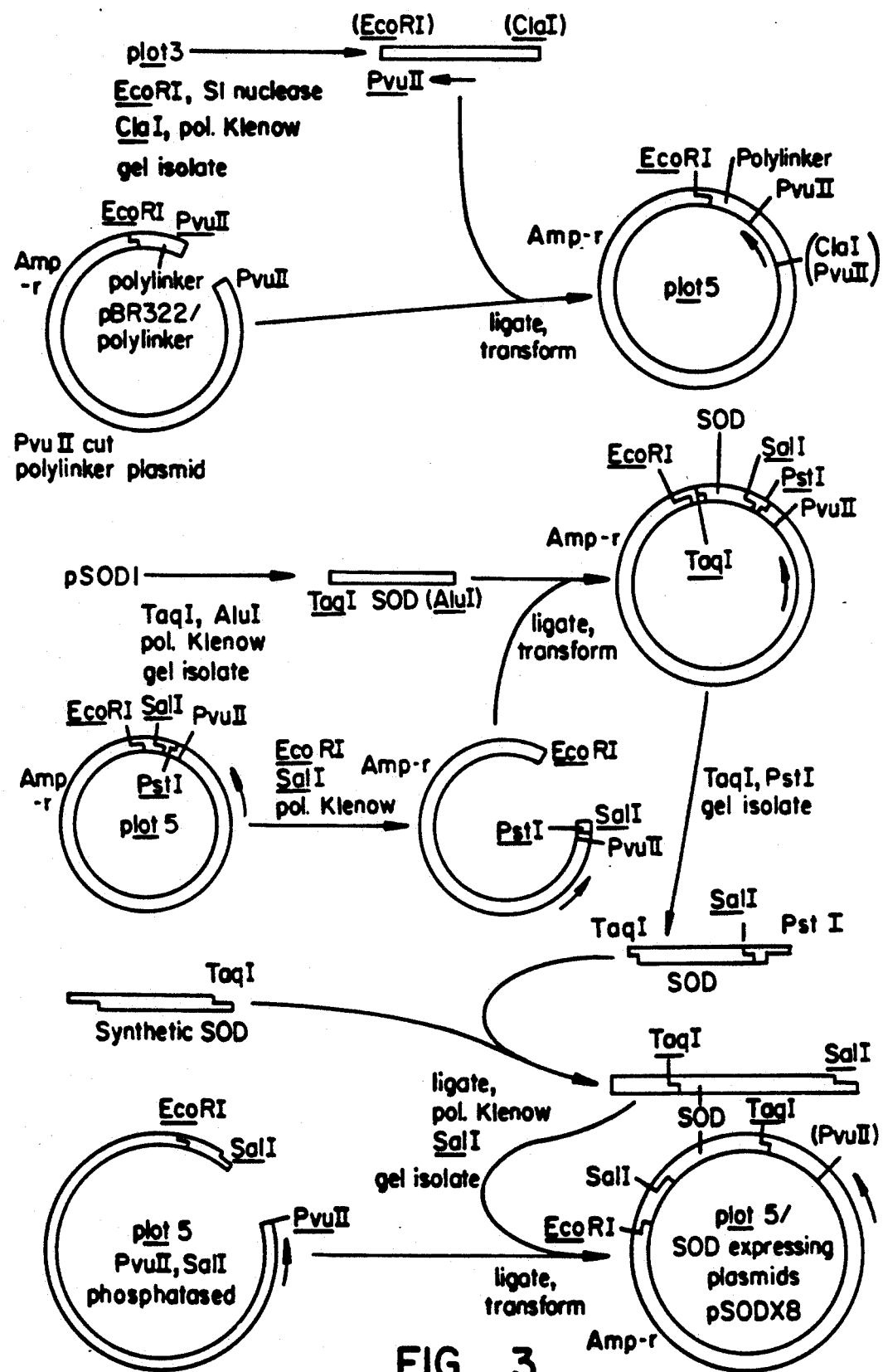
FIG._3.

Translation of hsod

```
      10                                         20
gly asp gly pro val gln gly ile ile asn phe glu gln lys glu
GGC GAC GGC CCA GTG CAG GGC ATC ATC AAT TTC GAG CAG AAG GAA
        *Sau 96 I                       *TaqI
                           30
ser asn gly pro val lys val trp gly ser ile lys gly leu thr
AGT AAT GGA CCA GTG AAG GTG TGG GGA AGC ATT AAA GGA CTG ACT
        *Sau 96 I
      40                                         50
glu gly leu his gly phe his val his glu phe gly asp asn thr
GAA GGC CTG CAT GGA TTC CAT GTT CAT GAG TTT GGA GAT AAT ACA 60
ala gly cys thr ser ala gly pro his phe asn pro leu ser arg
GCA GGC TGT ACC AGT GCA GGT CCT CAC TTT AAT CCT CTA TCC AGA 70                                         80
lys his gly gly pro lys asp glu glu arg his val gly asp leu
AAA CAC GGT GGG CCA AAG GAT GAA GAG AGG CAT GTT GGA GAC TTG
                             90
gly asn val thr ala asp lys asp gly val ala asp val ser ile
GGC AAT GTG ACT GCT GAC AAA GAT GGT GTG GCC GAT GTG TCT ATT 100                                         110
glu asp ser val ile ser leu ser gly asp his cys ile ile gly
GAA GAT TCT GTG ATC TCA CTC TCA GGA GAC CAT TGC ATC ATT GGC 120
arg thr leu val val his glu lys ala asp asp leu gly lys gly
CGC ACA CTG GTG GTC CAT GAA AAA GCA GAT GAC TTG GGC AAA GGT 130                                         140
gly asn glu glu ser thr lys thr gly asn ala gly ser arg leu
GGA AAT GAA GAA AGT ACA AAG ACA GGA AAC GCT GGC AGT CGT TTG 150         153
ala cys gly val ile gly ile ala gln OC
GCT TGT GGT GTA ATT GGG ATC GCC CAA TAA ACATTCCCTTGGCTGTAGTCT
GAGGCCCCTTAACTCATCTGTTATCCTGCTAGCTC-
                                *AluI
```

Translated Mol. Weight = 14893.03

FIG._4.

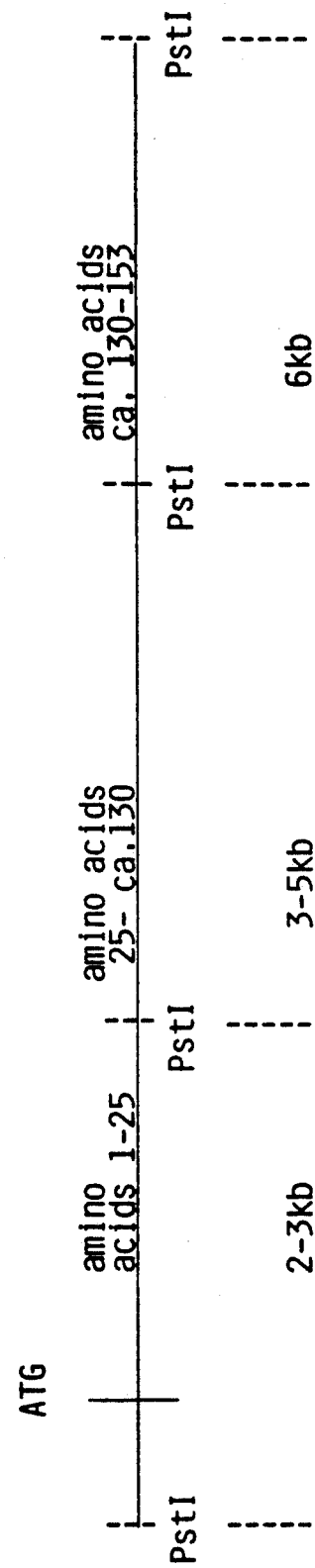
```
CTGCAGGCGTCTGGGGTTTCCGTTGCAGTCCTCGGAACCAGGACCTCGGCGTGGCCTAGCGAGTT       Met
                                                                      ATG
Ala Thr Lys Ala Val Cys Val Leu Lys Gly Asp Gly Pro Val Gln Gly Ile Ile
GCG ACG AAG GCC GTG TGC GTG CTG AAG GGC GAC GGC CCA GTG CAG GGC ATC ATC
Asn Phe Glu Gln Lys
AAT TTC GAG CAG AAG  GCAAGGGCTGGGACGGAGGCTTG
        EXON <------|  |------> INTRON
```
FIG._5.
FIG._6.

SUPEROXIDE DISMUTASE CLONING AND EXPRESSION IN MICROORGANISMS

This application is a continuation of application Ser. No. 931,920, filed Nov. 14, 1986 which is a continuation of Ser. No. 609,412, filed May 11, 1984 (abandoned).

DESCRIPTION OF SPECIFIC EMBODIMENTS

1. Field of the Invention

Superoxide dismutase ("SOD") is in fact a variety of different enzymes found in most living organisms. One function is mammals is to destroy superoxide, a material naturally produced during phagocytosis. The superoxide dismutases are characterized in families based on the metal associated with the enzyme, where the metals vary amongst iron, manganese, copper and copper-zinc. Superoxide dismutase, e.g., from bovine liver, has found clinical use, particularly humans. Other utilities include scavenging superoxide anions due to exposure of a host to various superoxide-inducing agents, e.g, radiation, paraquat, etc.; prophylaxis or therapy for certain degenerative diseases, e.g., emphysema; food preservation; and the like.

It is therefore important that stable supplies of physiologically acceptable superoxide dismutase be made available, particularly for use in vivo as an anti-inflammatory agent or for other therapeutic purposes. For human application it would be preferable to employ the homologous enzyme to prevent or minimize possible immune response. By employing recombinant DNA techniques, there is the opportunity to produce products efficiently, which have the desired biological activities of superoxide dismutase, such as immunological and enzymatic activities.

2. Description of the Prior Art

The amino acid sequence of human erythrocyte Cu-Zn superoxide dismutase is described in Jabusch et al., *Biochemistry* (1980) 19:2310–2316 and Barra et al., *FEBS Letters* (1980) 120:53–55. Bovine erythrocyte Cu-Zn SOD is described by Steinman et al., *J. Biol. Chem.* (1974) 249:7326–7338. A SOD-1 cDNA clone is described by Lieman-Hurwitz et al., *Proc. Natl. Acad. Sci. USA* (1982) 79:2808–2811. Concerning the effect on efficiency of translation of varying the untranslated region upstream from the initiation codon, see Gheysen et al., *Gene* (1982) 17:55–63; Thummel et al., *J. Virol.* (1981) 37:683–697; and Matteucci and Heyneker, *Nucl. Acids Res.* (1983) 11:3113–3121.

SUMMARY OF THE INVENTION

Efficient production of polypeptides demonstrating the biological activity of human Cu-Zn superoxide dismutase is demonstrated by the preparation of cDNA of the major portion of the structural gene, linking to a mixture of adapters providing for varying sequences extending from the ribosomal binding site to degenerate nucleotides in the coding region, and insertion of the complete gene with its translational signals into an expression vector. Transformation of microorganisms results in efficient production of a competent polypeptide demonstrating biological activity of human Cu—Zn superoxide dismutase. The gene may be further used for combining with secretory and processing signals for secretion in an appropriate host.

Novel protocols are provided for enhancing expression of a polypeptide involving the use of mixtures of adapters having varying sequences flanking the initiation site for translation, i.e., in the region between the ribosomal binding site and translational initiation site and in the initial several 5'-codons of the polypeptide, where permitted by redundancy constraints of the genetic code.

Polypeptides acetylated at their N-terminus and methods for producing such acetylated polypeptides are also provided. By providing a particular acetylation signal sequence at the 5'-end of the structural gene for a desired polypeptide, the N-terminal amino acid will be acetylated when the gene is expressed in yeast. The acetylation signal sequence encodes for at least the first two N-terminal amino acids, where the first amino acid is either alanine or glycine, and the second amino acid is a polar amino acid, usually being threonine, serine or aspartate. Acetylation of human superoxide dismutase produced in yeast is demonstrated when the first two amino acids are alanine and threonine, respectively.

BRIEF DESCRIPTION OF THE DRAWINGS

FIG. 1 indicates the DNA linker sequence and a flow diagram showing its use;

FIGS. 2 and 3 are flow diagrams indicating the preparation of plot5/SOD.

FIG. 4 indicates the sequence of both the coding strand of human SOD cDNA (5'→3') and the resultant translation product.

FIG. 5 illustrates the sequence of the isolated human SOD gene described in the Experimental section hereinafter.

FIG. 6 is a restriction map of the isolated human SOD gene described in the Experimental section hereinafter.

DESCRIPTION OF SPECIFIC EMBODIMENTS

Methods and compositions are provided for the efficient expression of polypeptides demonstrating the biological activities of human Cu—Zn superoxide dismutase ("hSOD"). The methods employ a DNA sequence ("hSOD gene") encoding a substantial portion of the amino acid sequence of hSOD in conjunction with a translational initiation region optimized for expression in the expression host. The hSOD gene is inserted into an appropriate vector for expression in a host, conveniently under conditions which allow for secretion, so as to harvest the SOD product from the extracellular medium.

Methods and compositions are also provided for the N-terminal acetylation of hSOD and other polypeptides. Hereinafter, acetylation refers to addition at the amino terminus of polypeptides and proteins in contrast to modification of amino acid side chains, e.g., lysine, as is also observed naturally. Acetylation of polypeptides and proteins is useful for a number of reasons. Where the natural condition of the polypeptide includes acetylation, as is the case for cytoplasmic hSOD, methods of expression which include acetylation provide a product having the desired natural structure and conformation. Where the product finds pharmaceutical and/or in vitro or in vivo diagnostic use, the acetylated material will minimize or eliminate immunogenicity when administered to a host and/or exposed to biological samples. Also, acetylated polypeptides are likely to be more stable and resistant to degradation by proteases and thus enjoy a prolonged existance in the cell, blood or body and tissue fluids.

The structural gene for hSOD or other polypeptide includes an acetylation signal sequence at the 5'-end thereof, which signal sequence causes a yeast expression host to effect acylation. The acetylation signal sequence encodes at least the first two N-terminal amino acids in the polypeptide. The first amino acid will be either alanine, glycine or serine, while the second amino acid will be a polar or aromatic amino acid, usually being threonine, serine, aspartate or phenylalanine.

The amino acids may be the natural N-terminal amino acids normally present in the polypeptide to be expressed. This is the case with hSOD where the first two amino acids are alanine and threonine, respectively. Other naturally-acetylated proteins which may be expressed and acetylated in yeast include:

| Protein | Source | Signal Sequence |
|---|---|---|
| Cytochrome C | Human, Rhesus Monkey, Dog, Horse, etc. | GLY—ASP |
| Cytochrome C | Castor, Sesame, Mung-bean, etc. | ALA—SER |
| Glutamate dehydrogenase | Neurospora | SER—ASN |
| Calmodulin | Pig | SER—ALA |
| Myosin (light chain A2) | — | SER—PHE |
| ADH | Drosphila | SER—PHE |

The present invention is also useful for acetylating polypeptides and proteins which are not naturally acetylated. Acetylation may be achieved by joining the acetylation signal sequence to the 5'-end of the structural gene for the polypeptide. The acetylation signal sequence will encode for at least two amino acids (as described above), and may encode up to ten or more amino acids, preferably fewer than five amino acids. Fewer added amino acids is usually desirable to limit interference with or loss of a desired activity of the polypeptide. Conveniently, the signal sequence may be synthesized and joined to the structural gene using well known techniques.

As an alternative to adding the acetylation signal sequence to the structural gene, it will sometimes be possible to modify the 5'-end of the structural gene to substitute one or both of the first two amino acids of the polypeptide. Such modification may be accomplished by a variety of conventional methods. For example, the structural gene may be restricted near its 5'-end to remove a known number of nucleotides. A synthetic oligonucleotide may then be joined to the cohesive end remaining after restriction. The oligonucleotide will restore and substitute the base pairs as necessary to provide the desired acetylation signal sequence Alternatively, site-specific mutagenesis employing, e.g., phage M13, can be used to effect an appropriate modification to the 5'-end of the structural gene.

In order to prepare hSOD, it is necessary to have a DNA sequence which encodes for hSOD. One manner of achieving such sequence, is to clone cDNA from messenger RNA from cells which produce hSOD. Conveniently, human liver cells may be used for this purpose. After the cDNA is cloned, where the DNA coding sequence is unknown, but at least a partial amino acid sequence is known, one may then screen the cDNA with mixtures of probes having all of the possible variations of nucleotides encoding for the particular series of amino acid residues. The choice of the residues for which the sequence encodes is somewhat arbitrary, although the residues chosen will usually be selected to minimize the number of different sequences which must be synthesized.

For hSOD, conveniently a DNA sequence encoding for at least the amino acid residues 19 to 24 can be used, particularly a probe having at least about 15 bases and not more than about 20 bases, more conveniently about 17 bases. One may then restriction enzyme digest the clones which appear to hybridize with the labeled probes, fractionate the DNA fragments and repeat the hybridization, particularly by employing a second series of probes which hybridize to DNA sequences encoding for a different series of amino acid residues in hSOD. Conveniently, these amino acid residues may be 109 to 114. One or more clones may be found which are positive to both probes and these may be used as a source for cDNA encoding for at least a substantial proportion of hSOD.

Quite surprisingly, it was found that the amino acid sequences which have been published for hSOD differed in a significant number of residues from the amino acid sequence encoded for by the cDNA. Specifically, where the two published sequences differed (Jabusch et al., *Biochemistry* (1980) 19:2310–2316 and Barra et al., *FEBS Letters* (1980) 120:153–156), the correct assignments are: residue 11, aspartate; residue 17, isoleucine; residue 26, asparagine; residue 49, glutamate; residue 52, aspartate; residue 53, asparagine; residue 92, aspartate; residue 98, serine (see FIG. 4).

Because of the uncertainties of the effect on translation of the separation between the ribosomal binding site and the translational initiation codon, normally AUG, the subject method provides a technique for varying the distance and nucleotides separating the ribosomal binding site from the initiation codon. Usually, there are from about 6 to 15, more usually about 6 to 12 nucleotides in the spacer between the ribosomal binding site and initiation codon. As the base sequence downstream from the initiation site may also affect translation efficiency, the subject method also provides for variation of nucleotide sequence (but not length) within the initial several 5'-codons of the polypeptide as permitted by the redundancy constraints of the genetic code. Such degeneracy may intend up to 4 codons, more usually 2 codons, downstream from the initiation site.

A plurality of linkers are prepared where at least 2 nucleotides, usually at least 3 nucleotides, and not more than 10 nucleotides, usually not more than about 6 nucleotides, are varied to include members having each of the 4 nucleotides if within the spacer or 2, 3, or 4 nucleotides as permitted by genetic code redundancy if within the structural gene for the polypeptide. In addition, the linkers are prepared, having differing numbers of nucleotides, so as to provide a group of linkers differing not only in the sequence, but also in length. The difference in length can be achieved by removal of portions of the support during the linker synthesis and, if appropriate, continuing synthesis at a subsequent stage, so as to provide for linkers having a graduated number of sequence lengths. Usually, the mixture of linkers will vary in length by at least one nucleotide and not more than over a range of six nucleotides, usually not more than four nucleotides.

This can be conveniently illustrated where the absent bases are at the terminus. After each stage, a portion of the support is removed and the synthesis continued with the strands bound to the support, providing all four nucleotides (dNTP) at each stage. These single strands will then be hybridized to a single strand which is complementary in part, where the variable region will be an overhang. Thus, one will achieve a graduated series of linkers having overhangs differing in both their nucleotide sequences and lengths. At an appropriate point during subsequent hybridization, ligation or cloning operations the overhang region(s) is filled in to provide double-stranded material amenable to further manipulation. This is usually and preferably performed in vitro, e.g., using the Klenow fragment of DNA polymerase I; alternatively, in certain constructs the overhang could be cloned as a single strand with filling in occurring in vivo in the transformed or transfected host. Hybridization to a complementary strand can be achieved by having a 5'-sequence upstream from the variable nucleotide series which is complementary to a sequence present in the terminal sequence to which the linker is to be joined. The missing bases may then be filled in vitro or in vivo.

The linkers include within their sequence, at least a portion of the region between the ribosomal binding site and the initiation codon, preferably the nucleotides proximal to the initiation codon. The linker may also include the initiation codon and portions of the structural gene, the ribosomal binding site, and bases upstream from the ribosomal binding site, which may or may not include transcriptional regulatory sequences.

Usually the linker will be at least about 5 bases, more usually at least about 20 bases, and usually not exceeding about 200 bases, more usually not exceeding about 100 bases. Where the linker is greater than about 35 bases, it will usually be assembled by employing single stranded sequences of from about 10 to 35 bases, which have homology with only a part of a complementary strand, thus providing for complementary overlapping sequences with overhangs, so that the various single strands can be hybridized, ligated and the degenerate and/or variable length overhang filled in as indicated above to produce the desired linker having cohesive and/or blunt ends.

Where the structural gene has a convenient restriction site, usually not more than about 50 bases downstream from the initiation codon, a fragment containing the structural gene may be restricted and joined to a complementary cohesive terminus of the linker or may be filled in to provide a blunt-end terminus, which blunt end may be ligated to a blunt end of the linker. The linker is devised to ensure that the structural gene is complete and in reading frame with the initiation codon.

As indicated, in preparing the linker, one provides that there are a series of linkers which have a randomized series of nucleotides, that is, each of the four possible nucleotides in the coding strand (subject to the provision of genetic code limitations indicated above) and which are graduated in size, lacking one or more of the nucleotides defining the region intermediate or bridging the ribosomal binding site and initiation codon. These linkers which are prepared from single strands may be joined to other single or double DNA strands to provide for extended linkers, which may include not only the ribosomal binding site, but bases upstream from the ribosomal binding site. Alternatively, the linkers may be relatively small, beginning at a site internal to or adjacent to the ribosomal binding site and extending downstream to a site at the initiation codon or internal to the structural gene.

While the particular order of joining the various fragments to produce the constructs of this invention will usually not be critical, conveniently, the structural gene may be first joined to the linker. This DNA construct will include not only the structural gene, but also the ribosomal binding site and any additional nucleotides upstream from the ribosomal binding site. In addition, there will be substantial variety in the nucleotides and numbers of nucleotides between the ribosomal binding site and initiation codon. The subject DNA construct is inserted into an appropriate expression vector which has the necessary transcriptional initiation regulatory sequences upstream, as well as transcriptional termination regulatory sequences downstream from the insertion site of the subject DNA construct. Thus, the linker will be flanked at the 5'-end with transcriptional initiation regulatory signal sequences and at the 3'-end with at least a portion of a coding region and transcriptional and translational termination sequences. (5'- and 3'-intend the direction of transcription.)

After preparing the plasmid or viral DNA for introduction into an appropriate host (usually including at an appropriate stage in the manipulations filling in of the variable overhang region), the host is transformed or transfected, respectively, cloned, the clones streaked and individual clones selected for efficient expression by assaying for production of the desired product, e.g., hSOD. The number of clones to be screened to determine the various levels of production of the product will depend upon and be proportional to the degree of length variability and sequence degeneracy introduced into the synthetic linker. As exemplified in the present embodiment, with 4 length variables and 4-fold sequence degeneracy at each of 6 nucleotides in the linker, the number of possible recombinant sequences is 5440. Usually at least a few hundred, preferably several thousand or more, clones will be screened. Screening can be efficiently performed using Western blots (antibody detection of product) of host cell colonies or viral plaques transferred to filters of nitrocellulase or other suitable material. Alternatively, using electrophoresis and providing for a plurality of lanes, where each lane is an individual clone, an immediate and direct comparison can be made of which clones are most efficient in expression by visualization of staining intensity, autoradiography or Western blotting of the product band. This screen will usually be sufficient, although more quantitative immunoassays or enzyme assays can be employed, as appropriate.

If desired, the construct can be transferred to a different host which recognizes the regulatory signals of the expression construct or the expression construct modified by introduction at appropriate sites of necessary regulatory signals to provide for efficient expression in an alternative host.

If desired, the hSOD gene may be joined to secretory leader and processing signals to provide for secretion and processing of the hSOD. Various secretory leader and processing signals have been described in the literature. See for example, U.S. Pat. Nos. 4,336,336 and 4,338,397, as well as copending application Ser. Nos. 522,909, filed Aug. 12, 1983 and 488,857, filed Apr. 26, 1983, the relevant portions of which are incorporated herein by reference.

Of particular interest as hosts are unicellular microorganism hosts, both prokaryotes and eukaryotes, such as bacteria, algae, fungi, etc. In particular, *E. coli*, *B. sub-*

*tilis, S. cerevisiae, Streptomyces, Neurospora* may afford hosts.

A wide variety of vectors are available for use in unicellular microorganisms, the vectors being derived from plasmids and viruses. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers are present, which provide for different characteristics.

In addition to the markers, vectors will have a replication system and in the case of expression vectors, will usually include both the initiation and termination transcriptional regulatory signals, such as promoters, which may be single or multiple tandem promoters, an mRNA capping sequence, a TATA box, enhancers, terminator, polyadenylation sequence, and one or more stop codons associated with the terminator. For translation, there will frequently be a ribosomal binding site as well as one or more stop codons, although usually stop codons will be associated with a structural gene. Alternatively, these regulatory sequences may be present on a fragment containing the structural gene, which is inserted into the vector.

Usually, there will be one or more restriction sites conveniently located for insertion of the structural gene into the expression vector. Once inserted, the expression vector containing the structural gene may be introduced into an appropriate host and the host cloned providing for efficient expression of hSOD.

In some instances, specialized properties may be provided for the vector, such as temperature sensitivity of expression, operators or activators for regulation of transcription, and the like. Of particular interest is the ability to control transcription by exogenous means, such as temperature, inducers, corepressors, etc., where transcription can be induced or repressed by an exogenous compound, usually organic.

Where the hSOD is made intracellularly, when the cell culture has reached a high density, the cells may be isolated, conveniently by centrifugation, lysed and the hSOD isolated by various techniques, such as extraction, affinity chromatography, electrophoresis, dialysis, or combinations thereof. Where the product is secreted, similar techniques may be employed with the nutrient medium, but the desired product will be a substantially higher proportion of total protein in the nutrient medium than in the cell lysate.

The hSOD which is formed has substantially the same amino acid sequence as the naturally occurring human superoxide dismutase, usually differing by fewer than 5 amino acids, more usually differing by fewer than 2 amino acids. The recombinant hSOD ("r-hSOD") displays substantially the same biological properties as naturally occurring hSOD. The biological properties include immunological properties, where antibodies raised to authentic hSOD cross-react with r-hSOD. Furthermore, in common bioassays employed for hSOD, the r-hSOD product demonstrates a substantial proportion, usually at least about 10%, preferably at least about 50%, more preferably at least about 80%, of the enzymatic activity of the authentic hSOD, based on weight of protein. An illustrative assay technique is described by Marklund and Marklund, *Eur. J. Biochem.* (1974) 47:469–474.

The following examples are offered by way of illustration and not by way of limitation.

EXPERIMENTAL

Molecular Cloning of hSOD cDNA

Total RNA was prepared from an adult human liver by the guanidinium thiocyanate/lithium chloride method (Cathala et al., *DNA* (1983) 2:329–335). polyA RNA was used to synthesize double-stranded cDNA (Maniatis et al., *Molecular Cloning*, 213–242, Cold Spring Harbor, 1982) and this was passed over a Sepharose CL4B column to enrich for cDNAs of greater than 350bp (Fiddes and Goodman, *Nature* (1979) 281:351–356). The cDNA was inserted at the PstI site of plot4, a pBR322 derivative having the following sequence replacing the PstI-EcoRI site.

```
     PstI        HinfI                        AluI
1        GGTGAATCCGTAATCATGGTCATAGCTGTTTCCTGTGTGAAATTGTTATCCGCTC
         ACGTCCACTTAGGCATTAGTACCAGTATCGACAAAGGACACACTTTAACAATAGGCGAG
            HphI HindIIAluI
60   ACAATTCCACACATTATACGAGCCGATGATTAATTGTCAACAGCTCATTTCAGAATATTT
     TGTTAAGGTGTGTAATATGCTCGGCTACTAATTAACAGTTGTCGAGTAAAGTCTTATAAA EcoRI
120  GCCAGAACCGTTATGATGCGG
     CGGTCTTGGCAATACTACGCCTTAA
```

The cDNA insertion employed the oligo-dG:dC tailing method (Maniatis et al., supra). *E. coli* strain D1210 was transformed with this mixture and transformants selected on L-agar containing 10μg/ml tetracycline (Kushner, S. R. (1978) In: *Genetic Engineering*, eds. Boyer, H. B. and Nicosia, S., (Elsevier/North Holland, Amsterdam) p. 17). Plasmid DNA constituting a liver cDNA library was prepared (Maniatis et al., *Molecular Cloning*, pp. 86–94, Cold Spring Harbor 1982) directly from approximately 62,000 recombinant colonies plated at a density of approximately 3,000 colonies per 9cm diameter Petri dish.

Isolation of r-hSOD Clones

Strain D1210 was retransformed with the liver cDNA library and about 40,000 clones were grown on nine 14cm diameter Petri dishes. After transfer of the colonies to nitrocellulose paper and chloramphenicol amplification of plasmid DNA, the cells were lysed and the filters prepared for hybridization (Ish-Horowicz and Burke, *Nucleic Acids Research* (1981) 9:2989–2998). Oligonucleotide probes were employed for screening by hybridization, with the probes consisting of enzymatically-radiolabeled, chemically-synthesized DNA molecules complementary to the mRNA encoding amino acid residues 19 to 24 of the protein (Jabusch et al., supra.; Barra et al., supra.); the mixture had the following sequences:

```
3' TTA AAA CTT GTT TTT CT 5'
       G   G   C   C
                   C
``` where all of the indicated possibilities for encoding the peptide sequence were prepared (32-fold degenerate).

The probes were labeled with $^{32}P$ to a specific activity of $1-3 \times 10^8$ cpm/μg and Millipore (0.45 μm) filtered before use. Filters were prehybridized for 6 hrs at 30° C. in 4×SSC, 2×Denhardts's solution, 40 mM sodium phosphate, pH 7.5, 300 μg/ml sonicated salmon testes DNA. Hybridization was for 20 hrs at 30° C. in the same solution containing $2 \times 10^6$ cpm/ml hSOD DNA probe (residues 19-24). Filters were washed in 4×SSC, once for 15 min at r.t. and twice for 15 min at 30° C., blotted dry and autoradiographed with an intensifying screen for 24 hrs at $-70°$ C.

Areas on the master plates that corresponded to duplicate positive signals were picked into L-broth and plasmid DNA prepared by the miniscreen procedure (Maniatis et al., Molecular Cloning, 178, 368-369, Cold Spring Harbor 1982). This DNA was cut with PstI and subjected to Southern blot analysis (Southern, J. Mol. Biol. (1975) 98:503-517) hybridizing initially with the previous labeled probes (amino acid residues 19-24) and then with additional radiolabeled probes derived from amino acid residues 109-114 and having the following sequences (all possible variations, 72-fold degenerate) present as a mixture:

```
3' CTA GTA ACA TAA TAA CC 5'
   G   G   G   G   G
               T   T
```

One plasmid pool (pSOD1) contained a cDNA insert of 520bp that hybridized with both probes and after colony purification, plasmid DNA was prepared from this clone and sequenced by the method of Maxam and Gilbert (*Proc. Natl. Acad. Sci. USA* (1977) 74:560-564) with the results shown in FIG. 4. The hSOD cDNA clone pSOD1 constitutes the coding region for amino acids 10-153 of hSOD, a single translational stop codon and a 3' untranslated region. Therefore, in the expression vector construct, the base sequence of the region encoding amino acids 1-9 is derived from the published amino acid sequence of hSOD (Jabusch et al., supra; Barra et al., supra) and synthesized chemically as a part of the variable linker segment (see below). Construction of Plasmid plot5

See FIGS. 2 and 3

Plasmid plot1, containing a hybrid trp-lac ("tac") promoter (DeBoer et al., *Proc. Natl. Acad. Sci. USA* (1983) 80:21-25) was constructed by gel isolating 15 the 180bp HgiA-TaqI fragment of ptrpL1 (Edman et al., *Nature* (1981) 291:503-506) and the 58bp HpaII-EcoRI fragment from pKB268 (Backman and Ptashne, Cell (1978) 13:65-71), and ligating these fragments to pBR322 digested with PstI and EcoRI. The resulting plasmid was used to transform strain D1210 and clones selected for tetracycline resistance. Plasmid plot3 was constructed by gel isolating the 155bp Fnu4HI-EcoRI fragment of plot1 containing the tac promoter, with the Fnu4HI site being made flush-ended using the Klenow fragment of DNA polymerase I ("pol I K" or "pol. Klen."), and the 18bp EcoRI-PstI polylinker fragment of IIAN7 of the following sequence:

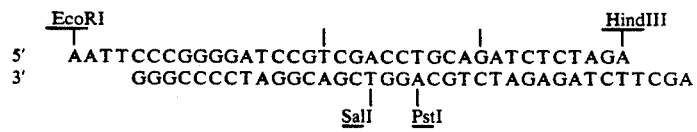

These fragments were ligated to gel purified pBR322 digested with EcoRI, flush-ended using pol I K, followed by digestion with PstI and gel purified. This ligation mix was used to transform strain D1210, selecting on L-agar plates-containing 10μg/ml tetracycline.

Plasmid plot5 was made by first constructing a plasmid containing the IIAN7 polylinker as an EcoRI-PvuII substitution in pBR322. To do this, plasmid IIAN7 was digested with HindIII, made flush-ended by filling in with pol I K and a synthetic, self-complementary, PvuII linker molecule (d(5'-CCAGCTGG-3')) ligated to the above-modified plasmid IIAN7. After digestion with EcoRI and PvuII, the resultant 44bp polylinker fragment (with 4-base overhangs) was gel isolated and cloned into pBR322 as an EcoRI-PvuII substitution.

Plasmid plot3 was digested with EcoRI and after phenol-chloroform extraction and ethanol precipitation, the protruding 5'-ends were made flush-ended by treatment with S1 nuclease (Palmiter, Biochemistry (1974) 13:3606-3615; Hallewell and Emtage, Gene (1980) 9:27-47). After phenol-chloroform extraction and ethanol precipitation, the DNA was digested with ClaI, made flush-ended by pol I K, and the 237bp fragment containing the tac promoter isolated by preparative polyacrylamide gel electrophoresis. This flush-ended tac promoter fragment was then inserted at the PvuII site of the pBR322 polylinker plasmid (see FIG. 3) and clones obtained in which the tac promoter directed transcription towards the ß-lactamase gene of pBR322.

Construction of plot5 Derivatives Expressing r-hSOD

The synthetic DNA molecules F(26), C(16), B(31), D(11), E(13) and 4(24) shown in FIG. 1, were synthesized by the phosphoramidite method. The single strand 4(24) was prepared by using all four bases, at each site where X is indicated. Furthermore, silica was withdrawn from the synthesis of the 24mer, such that single-stranded 21mers, 22mers, and 23mers are obtained in addition to the 24mers. After removal from the silica support, the four mixtures are combined in appropriate proportions to provide for equimolar amounts of each of the possible single strands. This mixture was treated as a single product in the subsequent steps.

Molecules F(26), C(16), B(31) and D(11) were mixed together in equimolar amounts and 10 μg phosphorylated using T4 polynucleotide kinase. After phenol-ether extraction, the additional nonphosphorylated synthetic DNA molecules 4(24) and E(13)were added, such that all fragments were equimolar. The equimolar mixture contained 13 μg of DNA in 133μl of 0.3×kinase buffer.

After annealing by cooling at a uniform rate from 70° C. to 20° C. over 60min, the single strands were ligated together with T4 ligase in 200 μl ligation mix at 14° C. for 4hrs, phenol-chloroform extracted, ethanol precipitated and the 5'-ends of 4(24) and E(13) phosphorylated using T4 polynucleotide kinase (Maniatis et al., supra). Preparative polyacrylamide gel electrophoresis was used to isolate the completely ligated 53 bp material having 5'- and 3'-overhangs.

The above purified fragment mixture was then ligated to the 460bp TaqI-PstI segment of the hSOD cDNA as shown in FIG. 1. This segment was itself constructed by isolating the 454bp TaqI-AluI hSOD fragment, making it flush-ended pol I K using and inserting it into plot5 between its EcoRI and SalI sites (see FIG. 3) which had been similarly made flush-ended. After preparation of plasmid DNA from this recombinant, the 460bp TaqI-PstI hSOD fragment was isolated by preparative polyacrylamide gel electrophoresis. After extraction and precipitation, the 515bp fragment resulting from the joining of the synthetic fragment to the 460bp TaqI-PstI hSOD fragment was filled in with pol I K (525–528 bp) and then digested with SalI and the resulting 519–522 bp hSOD fragment isolated by polyacrylamide gel electrophoresis. This fragment was then inserted into plot5 which had been digested with PvuII and SalI and then treated with alkaline phosphatase. The resulting plasmids were used to transform strain D1210. Recombinants obtained after transformation of strain D1210 were selected on L-agar containing 100 μg/ml ampicillin to give a set of clones (designated plot5/SOD) with variable SOD expression.

r-hSOD Expression and plot5/SOD Plasmid Selection

For analysis of total E. coli proteins by SDS-polyacrylamide gel electrophoresis, overnight cultures were diluted 30-fold into 1 ml of L-broth and grown shaking at 37° C. for 90 min. to an O.D.$_{650}$ of about 0.2. IPTG (isopropylthiogalactoside) was added to a final concentration of 2 mM and the cultures incubated an additional 3 hrs. After centrifugation, the cell pellet was resuspended in 50 μl of gel loading buffer (Laemmli, Nature (1970) 227:680–685) and lysed by repeating the following procedure 3×: Freezing for 1 min., boiling for 2 min., vortexing for 10 sec.

After electrophoresis resolution (Laemmli, supra) the protein bands were stained with Coomasie blue and the amount of SOD produced by each clone estimated; these results were then confirmed using Western blots with antibody to authentic human SOD. Over three hundred clones were analyzed and exhibited levels of SOD expression varying from little or none to amounts estimated to be 5–10% of the total soluble cellular protein. Results for two of the over three hundred clones are presented in Table 1, along with the particular sequence for DNA molecule 4(24) as determined by the method of Maxam and Gilbert, supra.

TABLE 1

| | Sequence and Levels of SOD Production in E. coli | | | |
|---|---|---|---|---|
| Clone | Sequence: 5'-XXXX ATG | GCX | ACX | Approximate Weight Percent of Total Protein |
| pSODx8 | AACA | A | G | 5% |

TABLE 1-continued

| | Sequence and Levels of SOD Production in E. coli | | | |
|---|---|---|---|---|
| Clone | Sequence: 5'-XXXX ATG | GCX | ACX | Approximate Weight Percent of Total Protein |
| pSOD11 | GTAT | T | G | 10% |

SOD assays were performed using the pyrogallol method (Marklund and Marklund, supra). The reaction mixtures employed 0.2 mM pyrogallol in assay buffer and reaction rates were determined over a 5 min. period using a Hewlett-Packard 8450 spectrophotometer at 420 nm. Four different assay samples were prepared: soluble E. coli extracts; authentic hSOD; and each of the prior samples pre-incubated with rabbit antibody to authentic hSOD. Each sample was incubated in a cuvette for 1 min. at 25° C. before adding the pyrogallol and assaying at 25° C. The antibody samples involved a preincubation of 10 min. at room temperature in assay buffer with 5 μl of antibody. These conditions were found to be sufficient to inactivate 100 ng of pure hSOD.

The following Table 2 indicates the results for one of the clones examined (pSOD×8):

TABLE 2

| Enzymatic Activity of Human Cu—Zn SOD Produced in E. Coli (strain D1210 (pSODX8)) | |
|---|---|
| Enzyme Preparation | Units SOD/mg Protein |
| pure Human Cu—Zn SOD | 15,384 |
| pSODX8 protein extract | 3,107 |
| pSODX8 protein extract preincubated with rabbit anti-human SOD antibody | 685 |
| plot5 protein extract | 470 |
| plot5 protein extract preincubated with rabbit anti-human SOD antibody | 485 |

These data indicate that approximately 15% of the total soluble cellular protein was hSOD (assuming that the pure human Cu-Zn SOD used as a reference was fully active). Taken together with the electrophoretic data (see above) indicating that 5–10% of total soluble cellular protein migrated as hSOD, it appears that a substantial fraction, probably a majority of the hSOD produced is active.

The correct sequence of the cloned gene was determined by the method of Maxam and Gilbert, supra. In addition, the first twelve amino acids at the N-terminus were determined by automated Edman degradation. The detected sequence of amino acids was as follows:

ALA—THR—LYS—ALA—VAL—(CYS-)—VAL—LEU—LYS—GLY—ASP—GLY—

The first ALA residue detected was present at a molar concentration approximately equal to that of the input peptide indicating the absence of a blocked amino terminus. The CYS residue was not detected by the method of amino acid analysis used, but its presence was inferred from the nucleotide sequence.

Thus, the (N-formyl-) methionine was removed from the bacterial expression product and the material had the correct amino acid sequences, i.e, identical to that reported for cytoplasmic hSOD residues 1-10, but the N-terminal ALA residue was not acetylated. Furthermore, the polypeptide made in E. coli migrated more slowly than the natural protein in 1% agarose gel (pH 8.6) electrophoresis which detects differences in charge (Corning Universal electrophoresis film, stained according to Clausen, *Immunochemical Technique*, p. 530-531), also indicating lack of acetylation. In addition, analysis of tryptic peptides of both the bacterial hSOD polypeptide and the purified, authentic (acetylated) natural protein revealed that all tryptic peptides were identical, except the bacterial N-terminal peptide which migrated differently, i.e., with a charge expected for a peptide lacking the N-acetyl group.

Expression in Yeast

For transfer of the r-hSOD gene to a yeast vector, the plot5/SOD plasmid clones were screened for an NcoI restriction site at the 5'-end of the coding region. For those plasmids where the variable nucleotides present 5' to the ATG initiation codon are CC, the sequence CCATGG provides an NcoI site. Clones were screened, and one was selected and designated phSOD.

The plasmid phSOD was digested with NcoI and SalI and a 550bp fragment obtained, which included 1 nucleotide untranslated at the 5'-terminus and the entire coding region for hSOD. pPGAP (a yeast expression vector carrying the GAP promoter, prepared as described below) was digested with NcoI and SalI followed by treatment with alkaline phosphatase, and the SalI-NcoI fragment substituted for the NcoI-SalI fragment in pPGAP to provide pPGAPSOD. BamHI digestion of pPGAPSOD resulted in a 2 kb fragment which was gel isolated and inserted into the BamHI site of pC1/1 and pC1/1 GAL4/370, to yield plasmids pC1/1GAPSOD and pC1/1GALGAPSOD, respectively.

Plasmid pC1/1 is a derivative of pJDB219 corresponding to bacterial plasmid pMB9 in pJDB219 was replaced by pBR322 in pC1/1. For preparing an expression vector having secretory and processing signals, see U.S. application Ser. No. 522,909. Plasmid pC1/1GAL4/370, a regulatable yeast expression vector containing the GAL1/GAL10 regulatory region (controlled by the GAL4 gene expression product) is prepared as described below.

Plasmids pC1/1GAPSOD and pC1/1GALGAPSOD were transformed into yeast strain 2150-2-3 (available from Lee Hartwell, University of Washington) as described previously (Hinnen et al. ,Proc. Natl. Acad. Sci. USA (1978) 75:1929-1933), with the results of expression set forth in the following Table 3.

TABLE 3

| Expression of Human SOD in Yeast Strain 2150 | | |
|---|---|---|
| Plasmid | Carbon Source | SOD[2] μg/mg protein |
| pC1/1 | g, L[1] | 0 |
| pC1/1GAPSOD | g, L | 148 |
| pC1/1GALGAPSOD | g, L | 0.4 |
|  | gal | 68 |

[1]All cultures grown in Minus Leucine media with 2% lactic acid, 3% glycerol with or without 2% galactose to late log or early stationary phase.
[2]Determined by RIA.

hSOD levels were measured using a standard radioimmunoassay with iodinated authentic hSOD as standard. Constitutive synthesis from the GAP promoter leads to very high levels of hSOD production, of the order of 10-30% of the total cell protein. The induction with galactose works almost as well, yielding about 7% of the cell protein as hSOD.

When hSOD is produced at these high levels, it is usually necessary to provide zinc and copper ion to the product protein as a prosthetic group in order to recover full enzymatic, i.e., catalytic, activity, e.g., by dialysis against 1 mM solutions of both zinc and copper sulfate. Alternatively, zinc and/or copper ion may be included in ten growth media; this method also provides a means of selecting for strains producing high levels of hSOD and/or avoiding the loss of plasmid vectors expressing hSOD in otherwise non-selective media.

Construction of pPGAP pGAP1, a plasmid prepared by insertion of a HindIII fragment containing the GAPDH gene GAP49 (Holland and Holland, *J. Biol. Chem.* (1979) 254:5466-5474) inserted in the HindIII site of pBR322, was digested with HinfI and a 500bp fragment isolated. The fragment was resected with Ba131 to remove about 50 or 90 bp, followed by ligation with HindIII linkers and digestion with HindIII. pBR322 was digested with HindIII, followed by treatment with alkaline phosphatase and the about 450 or 410bp fragment inserted to provide pGAP128.

pGAP128 was digested with HindIII, the fragment made blunt-ended with the Klenow fragment and dNTPs and the resulting 450 bp fragment isolated by gel electrophoresis. This fragment was inserted into SmaI digested plot5, which had been treated with alkaline phosphatase, to provide plasmid plot5pGAP128, which contained about −400 to +27bp of the GAPDH promoter and coding region.

Yeast expression vector pPGAP having a polyrestriction site linker between the GAPDH terminator and short promoter region was prepared as follows. Plasmid plot5pGAP128 was digested with BamHI and TaqI to yield an approximately 390bp BamHI-TaqI fragment having the −400 to −26bp of the GAPDH promoter. The BamHI-TaqI fragment was ligated to a synthetic fragment containing −25 to −1 bp of the GAPDH promoter and several restriction sites including NcoI and having the following sequence:

to provide a BamHI-SalI fragment, which was digested with BamHI and SalI and used to replace the BamHI-SalI fragment of BamHI-SalI digested pBR322 treated with alkaline phosphatase. After ligation, the plasmid pGAPNRS was obtained which was digested with BamHI and SalI to provide a 400bp BamHI-SalI fragment which was gel isolated. This fragment was ligated to an about 900bp SalI-BamHI fragment containing the GAPDH terminator region and a short segment of 3' coding region and the resulting 1.4kb BamHI-BamHI fragment digested with BamHI. The SalI-BamHI GAPDH terminator fragment was obtained by SalI and BamHI digestion of pGAP2, a plasmid prepared by insertion of an about 3.3kb BamHI fragment containing the GAPDH gene GAP49 (Holland and Holland, supra) into the BamHI site of pBR322. Plasmids pGAP2 and pGAP1 were obtained as follows: A yeast gene library was prepared by inserting fragments obtained after partial digestion of total yeast DNA with restriction endonuclease Sau3A in lambda-phage Charon 28 (Blattner et al., *Science* (1977) 196:161-169). The phage library was screened with DNA complementary to the yeast GAPDH mRNA and the yeast GAPDH gene from one of these clones was subcloned as either an about 3.3kb BamHI fragment in the BamHI site of pBR322 (pGAP-2) or as an about 2.1 kb HindIII fragment in the HindIII site of pBR322 (pGAP-1).

pBR322 was digested with EcoRI and SalI, the termini blunt-ended and ligated to BamHI linkers, followed by BamHI digestion and the BamHI-BamHI 3.8 kb fragment gel isolated, recircularized by self-ligation, cloned and designated pBRΔR1-Sal. The 1.4 kb BamHI-BamHI fragment was inserted into the BamHI-digested, alkaline phosphatase treated pBRΔR1-Sal vector to provide the plasmid pPGAP of about 5.3 kb with the orientation in the opposite direction of the amp$^r$.

Construction of GAL Regulated Containing Plasmids

Plasmid pLGSD5 is prepared as described in Guarente et al., (1982) supra. The plasmid was manipulated as follows: After restriction with XhoI, the overhangs were filled in with the Klenow fragment of DNA polymerase I ("Klenow fragment"), ligated with EcoRI linkers (GGAATTCC) and then completely digested with EcoRI and Sau3A to provide a 370 bp fragment which was isolated by gel electrophoresis and included the intergenic sequence between GAL1 and GAL10 genes of yeast, and provides for the GAL4 regulation sequence of the GAL1 and GAL10 genes.

This fragment was inserted into pBR322 which had been completely digested with EcoRI and BamHI, followed by treatment with alkaline phosphatase to prevent oligomerization resulting in plasmid pBRGAL4.

Plasmid pBRGAL4 was completely digested with Sau3A, the overhangs filled in with the Klenow fragment, and the resulting blunt-ended fragment ligated with SalI linkers (CGTCGACG), followed by digestion with SalI and XhoI. The resulting 370 bp fragment was isolated by gel electrophoresis. This fragment has the original 370bp yeast GAL4 regulator sequence with XhoI and SalI termini.

The fragment was then cloned in the plasmid plot5. plot5 was prepared by inserting the 40 bp polylinker fragment of the following sequence

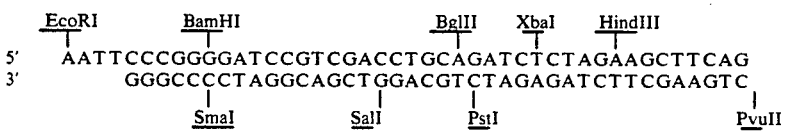

into pBR322 as an EcoRI-PvuII substitution followed by insertion of the trp-lac promoter (Russell and Bennett, Gene (1982) 20:231-245) into the PvuII site with transcription oriented toward the polylinker sequence. plot5 was completely digested with SalI, followed by treatment with alkaline phosphatase and the 370bp fragment inserted into plot5 to provide plasmid plot5-GAL4/370. This plasmid was then completely digested with BamHI and SalI to reproduce the individual fragment extended by 6bp of the polylinker fragment. This fragment was then ligated into pCl/1, which had been completely digested with BamHI and SalI followed by treatment with alkaline phosphatase to prevent recircularization. The resulting plasmid was designated pCl/1GAL4/370. The BamHI-SalI fragment is located in the pBR322 portion of the vector pCl/1.

The phSOD polypeptide made in yeast was shown to be identical to the natural human protein. Migration of hSOD made in yeast was identical to the protein in both polyacrylamide gel electrophoresis (with and without sodium dodecyl sulfate) and in agarose gel electrophoresis (see above). Moreover, when highly purified yeast polypeptide was subjected to twelve cycles of Edman degradation, the sequence was the same as that reported for the human protein (residues 1-10) made in E. coli set forth above. The level of detection, however, was only 5 to 10% of the expected level on a molar basis relative to protein input. This reduced detection level indicated that the N-terminal amino acid was blocked, i.e., probably acetylated. The result was confirmed by comparative analysis of tryptic peptides derived from yeast-produced hSOD and authentic acetylated human material which showed that all the expected trypic proteins were identical in the two samples including the N-terminal one, thus indicating the presence of acetylated N-terminal ALA in the yeast expression product.

Isolation of the Human SOD Gene

To isolate the human SOD gene, a bacteriophage lambda library representative of the human genome (R. Lawn et al. (1978) Cell 15:1157-1174) was screened with a radiolabelled DNA probe made from the human SOD cDNA. One million phage plaques were screened, and 13 positively hybridizing plaques were purified. Restriction endonuclease analysis of the phage DNAs indicated that there are at least 5 different genes, suggesting that there are other SOD related genes and gene products. One candidate for such a gene is the recently discovered extracellular Cu/Zn SOD (S. Marklund, (1982) Proc. Natl. Acad. Sci. USA 79:7634-7638). To distinguish the authentic cytoplasmic Cu/Zn SOD gene from the related ones we used synthetic DNA probes 5'-AATGCTTCCCCACACC-3' and 5'-CTCAGT-TAAAATGTCTGTTTG-3' corresponding to amino acid residues 19-26 and nucleotides 193-213 3' from the terminator codon in the 3' untranslated region, respectively. Only one of the 13 genomic DNAs hybridized with these probes, indicating that it is the authentic human cytoplasmic SOD gene. This was confirmed by DNA sequence analysis of the N-terminal region, as shown in FIG. 5 where the amino acid sequence determined by protein sequencing is confirmed. This also shows that no preprotein exists for SOD since an in-frame termination codon exists nine nucleotides 5' from the initiator methionine codon. As shown in FIG. 5, the human Cu/Zn SOD gene contains intervening sequences. The map of the SOD gene shown in FIG. 6 indicates that there is more than one intervening sequence.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising a functional vector for expression in yeast, said vector comprising a promoter operable in yeast operably linked to a DNA segment encoding human cytoplasmic Cu/Zn superoxide dismutase polypeptide, wherein said polypeptide comprises an acetylation signal sequence operable in yeast that enables N-terminal acetylation of said polypeptide by said yeast.

2. The DNA construct of claim 1 wherein said yeast is S. cerevisiae.

3. The DNA construct of claim 1, wherein said vector further comprises a second DNA segment which is 5' to said DNA segment encoding human cytoplasmic Cu/Zn superoxide dismutase polypeptide, wherein said second DNA segment is a transcriptional initiation regulatory element.

4. The DNA construct of claim 3, wherein said vector further comprises a third DNA segment which is 3' to said DNA segment encoding human cytoplasmic Cu/Zn superoxide dismutase polypeptide, wherein said third DNA segment is a transcriptional termination regulatory element.

5. A method for preparing an acetylated human cytoplasmic Cu/Zn superoxide dismutase, said method comprising:

growing transformed yeast in a nutrient medium, wherein said yeast comprises a DNA construct, said DNA construct comprising a functional vector for expression in yeast, said vector comprising a promoter operable in yeast operably linked to a DNA segment encoding human cytoplasmic Cu/Zn superoxide dismutase polypeptide, wherein said polypeptide comprises an acetylation signal sequence operable in yeast that enables N-terminal acetylation of said polypeptide by said yeast, and isolating said polypeptide.

6. The method of claim 5, wherein said yeast is S. cerevisiae.

7. The method of claim 5, wherein said vector further comprises a second DNA segment which is 5' to said DNA segment encoding human cytoplasmic Cu/Zn superoxide dismutase polypeptide, wherein said second DNA segment is a transcriptional initiation regulatory element.

8. The method of claim 7, wherein said vector further comprises a third DNA segment which is 3' to said DNA segment encoding human cytoplasmic Cu/Zn superoxide dismutase polypeptide, wherein said third DNA segment is a transcriptional termination regulatory element.

9. A transformed yeast comprising a DNA construct, wherein said DNA construct comprises a functional vector for expression in yeast, said vector comprising a promoter operable in yeast operably linked to a DNA segment encoding human cytoplasmic Cu/Zn superoxide dismutase polypeptide, wherein said polypeptide comprises an acetylation signal sequence operable in yeast that enables N-terminal acetylation of said polypeptide by said yeast.

10. The transformed yeast of claim 9 wherein said yeast is S. cerevisiae.

11. The transformed yeast of claim 9, wherein said vector further comprises a second DNA segment which is 5' to said DNA segment encoding human cytoplasmic Cu/Zn superoxide dismutase polypeptide, wherein said second DNA segment is a transcriptional initiation regulatory element.

12. The transformed yeast of claim 11, wherein said vector further comprises a third DNA segment which is 3' to said DNA segment encoding human cytoplasmic Cu/Zn superoxide dismutase polypeptide, wherein said third DNA segment is a transcriptional termination regulatory element.

* * * * *

UNITED STATES PATENT AND TRADEMARK OFFICE
CERTIFICATE OF CORRECTION

PATENT NO. : 5,252,476

DATED : October 12, 1993

INVENTOR(S) : HALLEWELL ET AL

It is certified that error appears in the above-indentified patent and that said Letters Patent is hereby corrected as shown below:

Column 7, between lines 2 and 3, insert the following:

-- Yeast strains which synthesize high levels of superoxide dismutase can be selected for by growing the yeast in at least 2.5 mM copper sulfate. --

Signed and Sealed this

Twentieth Day of December, 1994

Attest:

BRUCE LEHMAN

Attesting Officer     Commissioner of Patents and Trademarks